United States Patent
Kellnberger et al.

(10) Patent No.: US 10,750,950 B2
(45) Date of Patent: Aug. 25, 2020

(54) DEVICE AND METHOD FOR FREQUENCY-DOMAIN THERMOACOUSTIC SENSING

(71) Applicant: HELMHOLTZ ZENTRUM MUENCHEN DEUTSCHES FORSCHUNGSZENTRUM FUER GESUNDHEIT UND UMWELT (GMBH), Neuherberg (DE)

(72) Inventors: Stephan Kellnberger, Kuenzing (DE); Pouyan Mohajerani, Tehran (IR); Vasilis Ntziachristos, Graefelfing (DE)

(73) Assignee: Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 780 days.

(21) Appl. No.: 15/305,874

(22) PCT Filed: Apr. 23, 2015

(86) PCT No.: PCT/EP2015/058827
§ 371 (c)(1),
(2) Date: Oct. 21, 2016

(87) PCT Pub. No.: WO2015/162215
PCT Pub. Date: Oct. 29, 2015

(65) Prior Publication Data
US 2017/0042428 A1    Feb. 16, 2017

(30) Foreign Application Priority Data
Apr. 25, 2014   (EP) .................................... 14001492

(51) Int. Cl.
*A61B 5/00* (2006.01)
*A61B 1/00* (2006.01)
(Continued)

(52) U.S. Cl.
CPC .......... *A61B 5/0093* (2013.01); *A61B 5/0095* (2013.01); *A61B 5/14532* (2013.01);
(Continued)

(58) Field of Classification Search
CPC ... A61B 5/0073; A61B 5/0095; A61B 5/0093; A61B 5/0059; G01N 21/1702; G01N 21/17
See application file for complete search history.

(56) References Cited

U.S. PATENT DOCUMENTS 5,377,006 A    12/1994  Nakata
5,781,294 A    7/1998   Nakata et al.
(Continued)

FOREIGN PATENT DOCUMENTS

EP    2829871    1/2015
EP    2829872    1/2015
(Continued)

OTHER PUBLICATIONS

International Search Report and Written Opinion prepared by the European Patent Office dated Jun. 22, 2015, for International Application No. PCT/EP2015/058827.

*Primary Examiner* — Elmer M Chao
(74) *Attorney, Agent, or Firm* — Sheridan Ross P.C.

(57) ABSTRACT

The invention relates to a device (100) and a corresponding method for thermoacoustic sensing, in particular thermoacoustic imaging, the device (100) comprising: a) an irradiation unit (10) configured to generate electromagnetic and/or particle energy exhibiting a first modulation, the first modulation comprising at least one frequency and to continuously emit the energy towards a target (1), whereby acoustic waves are continuously generated in the target, the acoustic waves exhibiting a second modulation, the second modulation comprising the at least one frequency and/or a harmonic (Continued)

Figure 1:
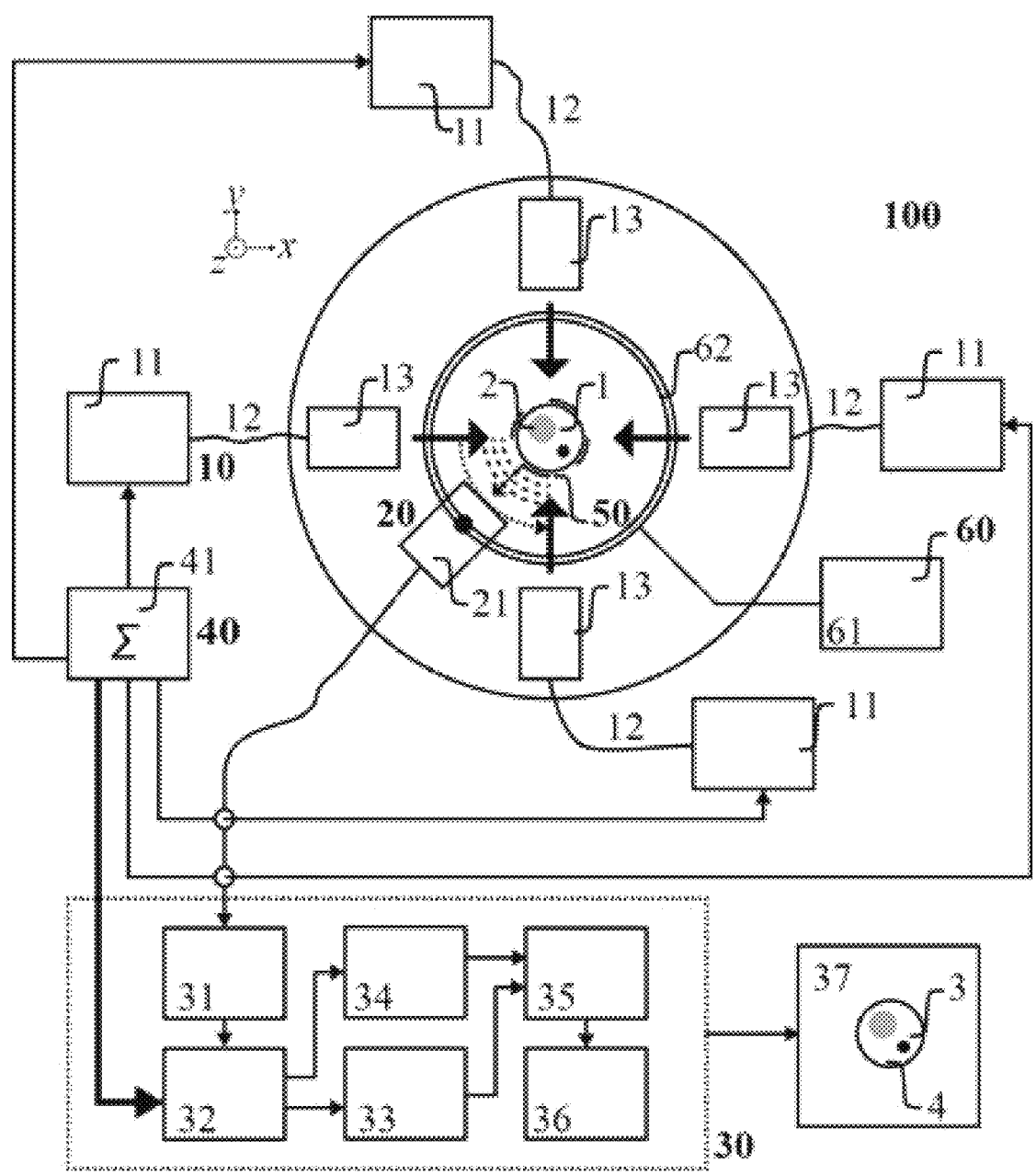

frequency of the at least one frequency; b) a detection unit (20) configured to simultaneously detect the acoustic waves exhibiting the second modulation while the energy exhibiting the first modulation is being continuously emitted towards the target (1); and c) a processing unit (30) configured to determine at least one thermoacoustic value of an amplitude and/or a phase of the second modulation of the acoustic waves at the at least one frequency and/or at a harmonic frequency of the at least one frequency. The invention allows for fast and economic thermoacoustic sensing, in particular imaging of a region of interest of an object.

16 Claims, 4 Drawing Sheets

(51) Int. Cl.
  *G01N 21/17*  (2006.01)
  *A61B 5/145*  (2006.01)
  *A61B 5/1455* (2006.01)

(52) U.S. Cl.
  CPC ...... *A61B 5/14546* (2013.01); *A61B 5/14551* (2013.01); *A61B 5/7228* (2013.01); *A61B 5/7257* (2013.01); *G01N 21/1702* (2013.01); *A61B 2576/00* (2013.01); *G01N 2021/178* (2013.01); *G01N 2021/1757* (2013.01); *G01N 2201/0625* (2013.01); *G01N 2201/0626* (2013.01); *G01N 2223/405* (2013.01); *G01N 2223/423* (2013.01); *G01N 2223/508* (2013.01)

(56) References Cited

U.S. PATENT DOCUMENTS

| | | | |
|---|---|---|---|
| 6,740,518 B1 * | 5/2004 | Duong | ............... G01N 27/3277 435/287.2 |
| 2011/0092824 A1 * | 4/2011 | Veen | ................... A61B 5/14551 600/477 |
| 2011/0190612 A1 | 8/2011 | McKenna et al. | |

FOREIGN PATENT DOCUMENTS

| | | | |
|---|---|---|---|
| JP | H10 160711 A | | 6/1998 |
| WO | WO2013167147 A1 * | | 5/2012 |

* cited by examiner

DEVICE AND METHOD FOR FREQUENCY-DOMAIN THERMOACOUSTIC SENSING

CROSS REFERENCE TO RELATED APPLICATIONS

This application is a national stage application under 35 U.S.C. 371 and claims the benefit of PCT Application No. PCT/EP2015/058827 having an international filing date of Apr. 23, 2015, which designated the United States, which PCT application claimed the benefit of European Patent Application No. 14001492.9 filed Apr. 25, 2014, the disclosures of each of which are incorporated herein by reference in their entirety.

The present invention relates to a device and a method for thermoacoustic sensing, in particular imaging, according to the independent claims.

Thermoacoustic signal generation is based on the photoacoustic effect, according to which ultrasonic waves are generated due to absorption of electromagnetic radiation by an object, e.g. a biological tissue, and a subsequent thermoelastic expansion of the object. Excitation radiation, for example laser light or radiofrequency radiation, can be pulsed radiation with short pulse durations or continuous radiation with varying amplitude or frequency.

WO 2013/167147 A1 discloses an apparatus and method for frequency-domain thermoacoustic tomographic imaging, wherein electromagnetic energy input into a region of interest in an object is continuously emitted with a predetermined input modulation and the mechanical wave response is converted into the frequency domain. A spatial distribution of absorbers in the region of interest is then reconstructed by considering the cross correlation from an input modulation signal with the mechanical wave response signals.

It is an object of the invention to provide a device and method for fast and economic thermoacoustic sensing, in particular thermoacoustic imaging, of a region of interest of an object.

The object is achieved by a device and method according to the independent claims.

A device for thermoacoustic sensing, in particular thermoacoustic imaging, according to an aspect of the invention comprises: a) an irradiation unit configured to continuously emit electromagnetic and/or particle radiation exhibiting a first modulation comprising at least one frequency and to irradiate a region of interest of an object with the continuously emitted radiation, whereby acoustic waves are continuously generated in the region of interest, the acoustic waves exhibiting a second modulation consisting of modulation components of frequencies corresponding to the at least one frequency of the first modulation and/or a harmonic frequency of the at least one frequency of the first modulation, b) a detection unit configured to simultaneously detect the acoustic waves exhibiting the second modulation while the region of interest is being irradiated with the radiation exhibiting the first modulation, and c) a processing unit configured to determine at least one thermoacoustic value of an amplitude and/or a phase of each component of the second modulation of the acoustic waves at each frequency contained in the first modulation and/or at a harmonic frequency of the at least one frequency contained in the first modulation and to derive at least one property of the region of interest based on the determined thermoacoustic values of amplitudes and/or phases.

A method for thermoacoustic sensing, in particular thermoacoustic imaging, according to another aspect of the invention comprises the following steps: a) continuously emitting electromagnetic and/or particle radiation exhibiting a first modulation comprising at least one frequency and irradiating a region of interest of an object with the continuously emitted radiation, whereby acoustic waves are continuously generated in the region of interest, the acoustic waves exhibiting a second modulation consisting of modulation components of frequencies corresponding to the at least one frequency of the first modulation and/or a harmonic frequency of the at least one frequency of the first modulation, b) simultaneously detecting the acoustic waves exhibiting the second modulation while the region of interest is being irradiated with the radiation exhibiting the first modulation, and c) determining at least one thermoacoustic value of an amplitude and/or a phase of each component of the second modulation of the acoustic waves at each frequency contained in the first modulation and/or at a harmonic frequency of the at least one frequency contained in the first modulation and deriving at least one property of the region of interest based on the determined thermoacoustic values of amplitudes and/or phases.

A preferred aspect of the invention employs a first modulation that consists of at least two modulation components of distinct frequencies. Correspondingly, the second modulation of the detected acoustic waves contains a number of distinct acoustic wave frequencies that are generated in response to the emitted first modulation.

A preferred aspect of the invention is based on the approach to employ continuous excitation of a region of interest (ROI) of an object, also referred to as medium, target or tissue, with transient electromagnetic energy (EME) or transient particle radiation to sense or image the object. Preferably, the intensity and/or the frequency of continuously emitted electromagnetic radiation or particle radiation is modulated, i.e. changed over time, at multiple distinct modulation frequencies, whereupon within the medium acoustic wave responses are generated exhibiting a modulation comprising acoustic wave components at multiple distinct frequencies corresponding to the multiple distinct modulation frequencies of the excitation radiation and/or harmonic frequencies thereof. The generated acoustic waves, in particular their components at the multiple distinct frequencies, are being continuously detected simultaneously, i.e. at the same time, while the medium is being continuously irradiated with the modulated electromagnetic radiation or transient particle radiation, respectively. Accordingly, there is no time dependence between the excitation and the detection of an acoustic wave response. This is why the excitation and detection approach, on which the present invention is preferably based, can also be referred to as "steady-state detection". This is in contrast to the system and method disclosed in WO 2013/167147 A1 which require a frequency sweep and a time-correlation of emitted and dependent components. Preferably, amplitude and/or phase of the acoustic wave components at the multiple distinct frequencies are processed in order to derive information associated with the medium excited by the EME or particle radiation, respectively. This processing can be applied to measure or sense at least one property of the medium or to generate an image thereof. The term "sensing" implies the measurement of properties in a medium. The term "imaging" relates to derive a representation of the spatial distribution of properties in a medium.

Preferably, electromagnetic energy relates to any electromagnetic radiation or near-field coupling, including radiofrequency and microwave (3 kHz to 300 GHz), millimeter waves/terahertz, IR, NIR and visible light, UV light and higher energies including X-ray, gamma-rays. Alternatively, transient energy can also be provided by means of particle beams comprised of proton, positron, neutron, electron beams, ion beams which are for example used in radiation therapy, and atoms or molecule beams. Preferably, the term "transient energy" relates to energy that changes one of its properties, in particular intensity and/or frequency and/or phase, over time.

The device and method according to a preferred aspect of the invention employ multiple distinct frequencies. The term "frequency" generally refers to the pattern of change for the transient EME or particle radiation. The actual modulation of the exciting electromagnetic or particle radiation does not necessarily have to be of sinusoidal form in order to have one defined frequency. It can be any transient and or periodic signal. This signal can be approximated by multiple distinct frequencies through the Fourier Transform, or modelled via wavelets or other decomposition method. The term "frequency" is used therefore to describe any transient EME field, transient energy or particle wave of any shape and/or time-profile. The term "frequencies" is also used to define frequency bands around a central frequency. Notwithstanding this generalization, and without loss of generality, the term "sinusoidal modulation" of the electromagnetic radiation or particle radiation is preferably used to denote the modulation of the electromagnetic radiation or particle radiation, respectively, at distinct and/or individual frequencies to exemplify aspects of the invention. Therefore, for means of clarity, in some examples the term frequency is used in the sense of a single sinusoidal modulated wave, but this implies also any generalization of frequency according to the disclosure herein. It is understood that the term "discrete frequencies" is used interchangeably to indicate waves at discrete sinusoidal modulation or more generally for multiple frequencies in the sense of a band or other grouping classification. These discrete frequencies can represent EME transients which are modulated directly at these frequencies or more complex EME transient patterns. The more complex patterns could be constructed in a way that they can be decomposed or approximated by these frequencies, for example in the sense of a Fourier transform.

In contrast to previous frequency domain approaches, the inventive device and method does not require chirps or cross-correlation detection. Instead, the device according to the invention measures complex values ($z=x+jy$, where z is a complex number and x and y are real numbers with the imaginary number $j=\sqrt{-1}$) which can be represented as the amplitude and phase of the resulting mechanical wave generated. The term "amplitude" relates to energy or vectors measured over time. The term "phase" denotes a shift between a feature of the excitation energy and a feature of the detected mechanical wave detected. In contrast to the concept of a "time-delay" employed in chirp implementations, the term "phase" within the sense of the present invention preferably denotes a spatial shift of a static field established in the medium. For example, for a sinusoidal modulated excitation field, phase relates to the angle of the sinusoidal ultrasound wave detected. This angle would be typically recorded and related to the angle of the excitation wave. However, phase is used more generally herein to denote any feature of the detected signal which varies with signal propagation.

Therefore, compared to previous frequency domain approaches including WO 2013/167147 A1, the inventive device and method does not represent a hybrid time-frequency domain thermoacoustic imaging device but relates to a pure frequency domain implementation performing imaging independent of time information. In particular, amplitude and phase of the detected thermoacoustic wave are used to reconstruct images of thermoacoustic sources disregarding any temporal indications of the signal.

In summary, the device and method according to the invention allows for faster and more economic thermoacoustic sensing and imaging of a region of interest of an object and, in particular, enables practical implementations with clinical, biological, chemical, environmental, industrial and other type of measurements.

Preferably, the first modulation of the electromagnetic or particle radiation corresponds to a modulation of the intensity or amplitude and/or the frequency of the continuously emitted radiation. For example, the intensity of the emitted radiation can be modulated at 5 MHz. It is, moreover, preferred that the second modulation of the generated acoustic waves corresponds to a modulation of the intensity or amplitude and/or the frequency of the continuously generated acoustic waves. In the aforementioned example, the generated acoustic waves are emitted at 5 MHz in the case of illumination with light, or upconverted frequencies (e.g. 10 MHz and more frequencies) in the case of electromagnetic radiation for example. The term "modulation" preferably relates to variation of a property, i.e. intensity or amplitude and/or frequency, of the excitation radiation or acoustic wave, respectively, over time.

Measurements determining a property of the medium (sensing), using a sensor, can be performed at single frequency. In addition, imaging methods performed with optical resolution optoacoustic (photoacoustic) imaging, by raster scan of a modulated light beam is possible at a single frequency. However implementations at at least two frequencies may be preferential for resolving e.g. absorption at multiple wavelengths simultaneously and performing fast spectroscopic imaging.

However imaging using acoustic resolution, i.e. when the imaging resolution and quality is determined by the acoustic detector characteristics (frequency, bandwidth or shape/geometry) is preferably performed at at-least two modulation frequencies, preferably at more than 5 frequencies, i.e. the modulation components correspond to two or more sinusoids at distinct frequencies. For example, the modulation components consist of in total five sinusoids having a frequency of 1, 2, 3, 4 and 5 MHz, respectively. Correspondingly, the detected ultrasound signals (second modulation) are emitted at the same 5 distinct frequencies in the case of light illumination and illumination exciting with energy absorption, or a number of upconverted frequencies, also referred to as harmonic frequencies, in radiofrequency and other electromagnetic excitation, i.e. when the excitation is based on amplitude and phase signals. Regarding the aforementioned aspects, in particular generation and/or detection, of upconverted frequencies, the content of the published international patent application WO 2013/167147 and the European Patent Applications EP 13 003 753.4 and EP 13 003 754.2 are incorporated by reference herewith.

According to another preferred embodiment, the first modulation and/or the second modulation correspond to a periodic modulation of the continuously emitted radiation and/or the continuously generated acoustic waves, respectively. The term "periodic modulation" preferably relates to a modulation comprising and/or being composed of a, preferably constant, recurring pattern of variation of the intensity and/or frequency of the radiation over a certain period of time. For example, the first modulation and/or the second modulation exhibit a rectangular, triangular or sawtooth shape, wherein the modulated radiation or acoustic wave, respectively, exhibits recurring rectangular-, triangular- or sawtooth-shaped intensity variation patterns. Although such simple patterns are preferred, a periodic modulation of the exciting radiation and/or of the generated acoustic waves exhibiting a more complex shape is possible and may be advantageous.

Preferably, the first modulation corresponds to a superposition of the two or more modulation components of distinct frequencies, i.e. the modulated signals at the at least two frequencies are concurrently emitted. In particular, the first modulation corresponds to a sum of the two or more sinusoids at the distinct frequencies. With the aforementioned example, the modulation is obtained by superimposing five sinusoids at the distinct frequencies, wherein the superposition—also referred to as Fourier synthesis—mathematically corresponds to a summation of the intensities of the respective sinusoids. In these embodiments, preferably all of the modulation components at the distinct modulation frequencies are simultaneously contained in the energy radiation emitted by the irradiation unit, so that the modulation components at distinct frequencies impinge upon the object at the same time. Accordingly, the modulation of the detected acoustic waves contains all the modulation components at these frequencies at the same time.

According to an alternative preferred embodiment, the first modulation corresponds to a consecutive modulation of the continuously emitted radiation by the two or more modulation components at distinct frequencies. That is, the energy radiation emitted by the irradiation unit is modulated such that each modulation component at a distinct modulation frequency is emitted one after the other, so that at a certain point in time only one modulation component at a certain frequency impinges upon the object. Accordingly, at a certain point in time the modulation of the detected acoustic wave contains only one of the modulation components at a certain frequency. As a result, the individual modulation components at distinct frequencies of the generated acoustic wave have to be detected consecutively.

It is also possible to combine the aforementioned embodiments such that the modulation of the continuously emitted radiation and/or the generated acoustic waves contains a first modulation part corresponding to a superposition of two or more modulation components of distinct frequencies and a second modulation part corresponding to a consecutive modulation of the continuously emitted radiation by two or more modulation components at distinct frequencies.

Preferably, the at least one derived property of the region of interest relates to an absorption, in particular an absorption coefficient, of radiation or energy coupling of the object which receives the continuously emitted radiation exhibiting the first modulation. It is also preferred that the derived property relates to a concentration of a substance, e.g. a tissue biomarker, in the object. Alternatively or additionally, the at least one derived property of the region of interest of the object corresponds to an image or a map of a spatial distribution of the at least one property of the object which is irradiated with the continuously emitted radiation exhibiting the first modulation.

According to further preferred embodiments, the distinct frequencies of the two or more modulation components are in a frequency range according to at least one of the following conditions: the distinct frequencies are in a frequency range below 15 MHz in the case that the at least one property shall be determined within a first maximum sensing depth within the object; the distinct frequencies are in a frequency range between 15 MHz and 50 MHz in the case that the at least one property shall be determined within a second maximum sensing depth within the object, the second maximum sensing depth being smaller than the first maximum sensing depth; and the distinct frequencies is in a frequency range above 50 MHz in the case that the at least one property shall be determined within a third maximum sensing depth within the object, the third maximum sensing depth being smaller than the second maximum sensing depth; and the distinct frequencies being in a frequency range corresponding to a detection bandwidth of the detection unit.

Preferably, the distinct modulation frequencies (f) of the irradiation EME or particle beam are chosen according to the size of the object. On the macroscopic scale (f<15 MHz, resolution>100 μm), whole organs and animals can be visualized due to the relatively low attenuation of ultrasound waves. As ultrasound penetration decreases with higher frequencies (approx. 0.6 dB/cm/MHz), imaging at higher modulation frequencies also limits the imaging depth. To visualize small objects (macro to microscopic level), high modulation frequencies (f>15 MHz) will be employed, while microscopic imaging will be performed at ultrahigh frequencies (f>50 MHz) with lower imaging depths. The distinct frequencies can be spaced over a large bandwidth, e.g. between 10 and 60 MHz to achieve multi-scale imaging. According to another embodiment of the invention, the distinct modulation frequencies are chosen to match the detection bandwidth of the ultrasound transducer of the detection unit. For example, when employing a 10 MHz PZT sensor with a detection bandwidth of 70%, excitation signals are set in the modulation bandwidth f=[6.5 MHz, 13.5 MHz] to enable efficient thermoacoustic signal sensing and imaging.

Alternatively or additionally, the distinct modulation frequencies can be selected in another way. Assuming depth profiling applications, for example glucose monitoring at different skin layers to avoid superficial interferences (one dimensional imaging), the frequency can be employed so as to optimize the SNR in phase detection as discussed below. Similarly, in two-dimensional or three-dimensional imaging applications the frequency or frequency band of the modulation frequencies can be selected so as to yield phase-discrimination that enables the desired resolution.

According to yet another preferred embodiment, the irradiation unit is configured to emit electromagnetic radiation and/or particle radiation at two or more different wavelengths. Preferably, the irradiation unit is configured to emit radiation consecutively at two or more different wavelengths, the radiation at each of the two or more different wavelengths exhibiting a first modulation consisting of two or more modulation components of distinct frequencies. Alternatively or additionally, the irradiation unit is configured to emit radiation simultaneously at two or more different wavelengths, the radiation at each of the two or more different wavelengths exhibiting a first modulation consisting of two or more modulation components of distinct frequencies. The term "wavelength" in the sense of the present invention relates to the wavelength and hence the radiation energy of the emitted electromagnetic radiation and/or particle radiation. In other words, the irradiation unit is configured to generate a multispectral illumination pattern at multiple (at least two) different wavelengths or radiation energy levels.

In analogy to a time domain implementation of multi-spectral optoacoustic tomography (MSOT) where the target is irradiated with multiple discrete wavelengths beams in a time shared fashion, a preferred approach of frequency domain multi-spectral optoacoustic tomography (FD- MSOT) comprises illuminating the object consecutively with a predefined first modulation pattern (consisting of modulation components at two or more distinct modulation frequencies) at two or more discrete wavelengths or energy levels of the emitted radiation. For example, at a first point in time the object is irradiated with radiation of a first wavelength/energy exhibiting a first intensity and/or frequency modulation consisting of modulation components at two or more distinct modulation frequencies, at a second (and later) point in time the object is irradiated with radiation of a second wavelength/energy exhibiting the first intensity and/or frequency modulation consisting of modulation components at the two or more distinct modulation frequencies, at a third (and even later) point in time the object is irradiated with radiation of a third wavelength/energy exhibiting the first intensity and/or frequency modulation consisting of modulation components at the two or more distinct modulation frequencies and so on. With this embodiment, the irradiation and detection steps preferably include imaging the target with transient EME exhibiting a defined intensity and/or frequency and/or phase modulation pattern while simultaneously detecting acoustic pressure signals at multiple projection angles, followed by a wavelength/frequency/phase shift of the EME altering the absorption characteristics of the region of interest.

It is to be noted that frequency domain multispectral optoacoustic tomography can also be implemented by simultaneously irradiating the object with a group of superimposed frequencies at multiple wavelengths.

According to a further preferred embodiment, multispectral illumination and detection is achieved by simultaneous irradiation of a tissue at multiple wavelengths/energies and multiple modulation frequencies. While TD-MSOT performs imaging at successive wavelengths, simultaneous FD-MSOT includes irradiating the target tissue with radiation exhibiting a modulation consisting components at multiple distinct frequencies (groups of frequencies) and multiple wavelengths/energies simultaneously, allowing thus for a particularly faster data acquisition to enable real-time tracking of physiological and molecular properties. In this case, the emitted radiation at each wavelength contains a group of different frequencies, each inducing a thermoacoustic signal with amplitude and phase information at each distinct frequency. It was found that these frequencies are ideally spaced as broadly as possible, for example for wavelength lambda1, frequencies at 1, 2, 3 . . . 7 MHz could be used. Then for wavelength lambda2, frequencies 1.1, 2.1, 3.1, . . . 7.1 MHz could be used, for wavelength lambda3 frequencies 1.2, 2.2, 3.2, . . . 7.2 MHz and so on. The particular frequency band could be of course spanning any acoustic frequency, from KHz to GHz, depending on the application. This is a particularly advantageous feature of FD-MSOT. By concurrently emitting wavelengths loaded at combinations of multiple frequencies, real-time multispectral observations can be achieved. This accelerates the scanning time and leads to accurate imaging since it eliminates motion artifacts common in time-domain methods that time-multiplex wavelengths.

This advantageous aspect is further preferred at imaging applications whereby imaging performance depends on the characteristics of the spatial characteristics of the energy absorbed at the first modulation and not of the acoustic detector. In this case, the requirement of multiple frequencies per wavelength may be waived. Instead, imaging can be performed by loading different energies (wavelengths) at different single frequencies, for example lambda 1 can be loaded onto 30 MHz, lambda 2 at 30.1 MHZ or 31 MHZ, lambda 3 at 30.2 or 32 MHZ and so on. As in acoustic resolution implementation the frequency range would depend on the particulars of the application. For example when focused light beams are used in raster scan mode for image formation, e.g. in optoacoustic microscopy, the detection process disclosed herein would be advantageous as it can allow sensing multiple wavelengths simultaneously. However due to the very small spot sizes achieved with focused light beams and the shallow tissue depths achieved in this case, high frequency components in the tens to hundreds of MHz for wavelength loading may be more appropriate. The detection process in this case can collect signals at the emitted frequencies and by using frequency unmixing (spectrum analysis, Fourier Transform) can record the tissue absorption contributions at each wavelength. We note that the frequency detection process may be also used to detect non-linear contributions, for example ultrasonic contributions generated by the interference or combination of vector signals (amplitude and phase components of the electromagnetic wave). An elaborated description of $2^{nd}$ harmonic excitation and the detection of the linear combination of more than 2 frequencies will be given further below.

According to yet another preferred embodiment, the detection unit is configured to detect acoustic waves, which are generated in the region of interest while the region of interest absorbs energy at the first modulation. A single detector is used for sensing approaches. Depending on the focusing characteristics of the detector, the detector can collect signal from an entire irradiated volume, or reject signals from some angles in order to offer sensing of a selected volume from the object absorbing the first modulation. A coupling medium may be used to interface acoustic waves to the sensor.

Alternatively or additionally, the detection unit is configured to detect acoustic waves generated in response to the first modulation at two or more different positions around the region of interest. For example, the detection unit comprises an acoustic wave detector which can be translated and/or rotated into different positions relative to the object. For example, when the detector is located in a first position at a first point in time, the detector detects the acoustic waves exhibiting the second modulation, and when the detector is located in a second position at a second (later) point in time, the detector detects the acoustic waves exhibiting the second modulation and so on.

Alternatively or additionally, the detection unit may be configured to detect the acoustic waves at two or more different positions being located on a straight line and/or a circular line and/or a cylindrically shaped area around the region of interest. For example, the detection unit comprises a number or a plurality of acoustic wave detectors being arranged at different positions relative to the object. Preferably, the different located detectors detect the acoustic waves exhibiting the second modulation simultaneously. This may be accomplished using an array of acoustic detectors and electronics collecting all signals in parallel. Acoustic wave detection can also be accomplished in a limited view mode where only a part of the object is covered by the detection unit. While full angular coverage provides higher image quality, image reconstruction can also be performed with projections encompassing only 60° or less of the scanned object. In addition the use of acoustic lenses may further define imaging characteristics by preferentially detecting signals from certain volumes.

Generally, the object can be stimulated at discrete modulation frequencies within a certain frequency band consecutively while the stimulating frequencies match the detection bandwidth of the detection unit, i.e. the ultrasound/mechanical pressure wave sensors. For example, illuminating tissue with an intensity modulated laser beam as the EME source using a PZT sensor with a cut off frequency of 5 MHz and an effective bandwidth of 4 MHz, discrete excitation frequencies can be arranged at f=[1, 2, 3, 4, 5] MHz. However as has been already explained, a more complex transient can be employed, consisting of multiple frequencies in the sense of frequencies captured after the Fourier transform of an excitation signal. Using ultrasound sensors of higher detection frequencies, the modulation frequencies of the EME source will be adapted to match the detection bandwidth of the sensors. Sound detectors can be piezoelectric-based transducers, capacitive micromachined ultrasound transducers (cMUT), interferometric transducers, transducers employing distortion of digital phase conjugation or holographic detection or any other sound detection principle.

According to yet another preferred embodiment, the device is designed as a handheld device that is adapted for being grasped and held with fingers and/or a hand in order to position the device onto an object under investigation and/or to move the device by hand relative to the object under investigation, in particular by positioning it onto or moving it along an exterior or interior surface of the object. The device can be used for imaging tissue (skin, subdermal structures, deep seated organs), as en endoscopic device imaging hollow organs (colonoscope, gastroscope, cervical scope or intravascular scope or as a sensor detecting signals from a volume or area.

Hereinafter, further additional or alternative aspects of the invention will be discussed.

Preferably, the device according the invention measures mechanical waves from a medium exposed to energy emitted by a source device. The irradiation or source unit is adapted to deliver EME of transient energy (such as transient electromagnetic energy across the electromagnetic spectrum) to the object, to stimulate mechanical responses of the tissue due to the photo/thermoacoustic effect. The energy emitted by the source device exhibits a modulation pattern at a frequency pattern, i.e. at single or multiple frequencies with a predetermined signal shape, for example a sinusoidal wave.

Preferably, the inventive device employs a detection unit capable of detecting mechanical pressure waves, also referred to as ultrasound signals, induced due to absorption of transient EME following thermoelastic expansion of the sample, also referred to as photoacoustic effect. The detection unit may comprise a single element ultrasound sensor or an array of sensors.

The device preferably further encompasses a signal acquisition and processing unit capable of processing the signals detected and computing at least one property of the medium measured. Based on this measurement, the processing unit derives a number, a graph, an image, a sound, another signal or similar.

One typical operation of the device can be to measure an environmental property, for example a chemical in water or glucose in blood. Another operation would be to provide an image (map) of energy absorption (particularly absorption of transient electromagnetic energy) within the object measured, using information from the acquired mechanical pressure waves/ultrasound signals.

Energy transmitted or coupled into the object by the source unit can be continuous or intermittent. The energy may be indefinitely on. However, preferably, the energy is switched on and off. This switching can be performed once per measurement or multiple times. For example, the energy at first modulation is emitted in the form of a pulse train with the on and off components of varying time duration (varying duty cycle). In this case, a preferred measurement will occur when the energy is emitted and there will be no measurement during the off intervals. These pulses are generally of different nature compared to the pulses used in time-domain optoacoustics. They are not short compared to the speed of sound, i.e. there is no time limitation of their duration and their duration does not affect the image resolution, as in the time domain. Additionally they carry modulated energy. The energy is preferably emitted at several distinct frequencies, but single frequency implementations are also possible. The multiple distinct frequencies can be transmitted in a time-shared mode or simultaneously. Pulsed emission of the first modulation may be used to multiplex different modulation patterns, different wavelengths or other energy spectra or for combining the inventive device with other methods that may interfere with the device. For exampie consequent pulses with very low off-energy intervals may be used to improve the scalability and dynamic range of detection. For example in the first pulse duration first modulation frequencies at 1-10 MHz may be on, in the second duration first modulation frequencies at the 10-30 MHz may be on and in the third another frequency range, for example 30-100 Mhz. In each pulse, the gain of the detector may be adapted to optimize the signal to noise ratio achieved on a per spectral range basis, therefore improving the dynamic range of the device. Pulsed emission can be also used to calibrate or normalize the sensor or imaging device, by providing measurements of background signals (interference) during off-energy intervals and measurements of second modulation signals and background and/or interference signal so that the effects of the background or interference signals may be removed. This removal can be based on subtraction between on and off signals, spectral unmixing or any other subtraction or filtering operation whereby information from the off-energy interval is employed into the removal process (for example a model based linear or non-linear subtraction). Yet another embodiment measures during selected intervals signals from a reference signal or target used for calibration purposes or quantification purposes. Measurement of a reference signal can be employed to monitor for a change of a device metric during the measurement or measure a known amount of substance or property in order to quantify a measured unknown amount of a substance or property. These operations are based on utilizing the measurements from the "calibration" interval to correct the experimental measurement by division or using a mathematical formula. Instead or parallel to consecutive excitation at multiple frequencies, the target can also be excited simultaneously by superimposing multiple discrete frequencies. This can be achieved by using a signal adder/waveform combiner (i.e. a device which allows for superimposing multiple signals at different frequencies) which stimulates the ROI in the target simultaneously, or by emitting a wavefront shape that contains the frequencies of interest. Compared to consecutive (time-shared) illumination and detection, the simultaneous approach allows for particularly fast, hardware efficient and safe thermoacoustic measurements.

Advantageously, the electromagnetic energy is in the optical wavelength range including at least one of infrared (IR), near-infrared (NIR), visible (VIS) and ultraviolet (UV) wavelength range. In this case, target tissue is illuminated with an intensity modulated optical source exhibiting a modulation pattern as described above.

Alternatively, the source device comprises a radiofrequency/microwave source emitting in the low frequency range (LF; f=30-300 kHz), medium frequency range (MF; f=300 kHz-3 MHz) and/or high frequency range (HF; f=3-30 MHz), also including lower frequencies (f<30 kHz) and higher frequencies (f>30 MHz).

Preferably, it should be understood herein that the energy employed for excitation purposes has an electromagnetic frequency implicit to the nature of radiation. Microwave radiation for example is assumed at 300 MHz to 300 GHz. Light emission is assumed at frequencies higher than $10^{14}$ Hz. A first modulation is then achieved by modulating this energy at frequencies in the Hz-GHz range, corresponding to exciting mechanical/acoustic waves from tissue.

Alternatively, transient radiative stimulation may be provided by means of higher energy beams, such as X-rays, gamma rays, or particle/ion beams such as proton, neutron, electron, positron beams of atoms and molecules.

The illumination pattern can exhibit different shapes and propagation modes, but preferably the modulation follows a sinusoidal, rectangular, triangle-shaped, or sawtooth shape. Using sinusoidal patterns, the induced thermoacoustic signal will be at the modulation frequency of the sinusoid. Using rectangular or triangle shaped illumination patterns, the spectral components of the generated thermoacoustic/optoacoustic signal will be at the odd harmonics with absence of even harmonics of the fundamental frequency. In principle, however, an excitation rich in frequency content is also possible, like frequencies over a range (band), e.g. over a 1 MHz band or over a 5 MHz band, can be used instead of using single or multiple discrete frequencies.

The irradiation or source unit is capable of generating/providing transient energy with defined modulation characteristics. According to a preferred embodiment, the source device is adapted for continuously emitting transient energy with a predetermined/known modulation frequency, such as an intensity modulated energy beam illuminating the target of interest. For example, the modulation type of the energy beam is a sinusoid at a discrete frequency $f_1$, or at multiple frequencies at $f_1, f_2, \ldots f_N$ (N∈□).

Furthermore, the source device is adapted to generate a superimposed signal containing multiple frequencies $f_1, f_2, \ldots f_N$ (N∈□) which allows for simultaneous illumination of the target with multiple frequency components. The multiple frequencies are preferentially spread across the bandwidth of the detector, in order to capture and generate images containing a rich content of spatial frequencies. The more the frequencies employed and the wider their spread, the more complete the reconstructed images.

For the so-called multispectral implementation, the irradiation or source unit configured to emit radiation at several different energy levels (e.g. wavelengths), for example as a wavelength tunable device or as an array of sources. Preferably, a group of modulation frequencies can be at one energy wavelength, another group of modulation frequencies can be at a second energy wavelength and so one. For example, when the source is a light source, distinct modulation frequencies at 2, 3, 4 and 5 MHz can be used for a wavelength 750 nm, frequencies at 2.1, 3.1, 4.1 and 5.1 MHz for 800 nm and frequencies at 2.2, 3.2, 4.2 and 5.2 MHz for 850 nm. Interleaving the frequencies for different wavelengths is advantageous when similar imaging performance in terms of capturing spatial frequencies is desired in all spectral bands (i.e. optical wavelengths). It is to be understood that when referring to a single and/or distinct modulation frequency, this may also imply a frequency band assuming that the mentioned frequency is a center frequency of this frequency band.

Illumination with multiple wavelengths/frequencies (FD-MSOT) can be employed to detect intrinsic features of the target, for example absorption, a spectral feature or a particular marker; for example a feature particle or molecule with a distinct absorption spectrum. For FD-MSOT of tissues for example, these features could be tissue chromophores/absorbing molecules such as oxy- or deoxy-hemoglobin, melanin, glucose, cytochrome and oxidated forms, bilirubin, various metabolites (NADH), iron etc. FD-MSOT can be combined with administered contrast agents or reporter markers such as dyes, fluorochromes, particles at different sizes (nano, micro) with different material properties (magnetic, carbon based, graphene, noble metals such as gold, silver) and also fluorescent dyes, microdots chromophoric markers and fluorescent conjugates. Readings from these agents or reporters can lead to the sensing, imaging and/or quantification of tissue biomarkers or of environmental, food, chemical and industrial/material features.

Advantageously, multispectral illumination enables molecular imaging of molecular probes at high sensitivity without the need of baseline measurements. Using spectral decomposition methods, the distribution of molecular agents can be precisely detected and determined by suppressing the optical contrast of the surrounding tissue.

The inventive device and method can further be used to quantify the distribution of a molecular marker/several molecular markers in real time using spectral un-mixing methods and algorithms. While time domain MSOT is limited in real time unmixing of molecular agents, the frequency domain multispectral optoacoustic implementation described herein allows for simultaneous excitation of at least one biomarker at several wavelengths. Using the measured/a-priori known absorption spectrum of the biomarker, FD-MSOT provides the capability to perform quantitative real-time visualization of the distribution of at least one biomarker in tissue. This is preferably achieved by illuminating the target simultaneously with multiple wavelengths at different groups of modulation frequencies followed by detection of amplitude and phase of the thermo/optoacoustic signals and multi-spectral unmixing in a processing unit.

Generally, image acquisition in the general form can be performed over an arbitrary group of frequencies exciting the tissue simultaneously. Reconstruction of the optical absorbers can be then performed using the amplitude and phase data via several approaches. Model-based methods rely on numerical discretization of the tissue volume and the partial differential equations involved to describe the relationship between acoustic measurements and the image using a linear model. This linear model is then regularized and the solution is obtained using convex optimization approaches. While highly accurate, such methods are somewhat time-consuming. Alternatively, we have additionally designed back-projection algorithms using fast Fourier transformation for inversion. Reconstruction in the k-space has further been developed, where the inversion is performed using inverse Radon transform. The back-projection methods are shown to have satisfactory performance while enabling real-time reconstruction due to their low computational complexity. Both model-based and back-projection schemes can operate for arbitrary detector configurations for uniform or non-uniform frequency samples.

Preferably, the image reconstruction algorithm performed by the processing unit can be combined with a photon propagation model, calculated for each wavelength/energy of the radiation and each modulation frequency, to provide quantitative images of opto/thermoacoustic sources. The modeling can be achieved, for instance, using finite-element modeling (FEM) of the diffusion approximation in the frequency domain, resulting in numerical solutions for the diffusive photon density waves (DPDW). FEM modeling can be performed given the location of a fixed or moving optical source. First step estimations of the optical absorption using thermoacoustic tomography can be used in a second step to improve the light propagation modeling accuracy. Monte-Carlo methods or higher order approximations of the radiative transport equation (RTE) can be used to model light propagation in non-turbid regions, such as regions partly filled with air (inter-luminal space, lungs, etc.) or regions partly filled with water or blood (such as veins).

Mechanical pressure signals are detected using at least one single element acoustic wave sensor or an array of acoustic sensing elements being sensitive to mechanical stress and/or sound pressure. The sensor and/or elements are preferably moveable relative to the object, for example translated or rotated around or inside the object to achieve multi-projection signal acquisition at different angles around the object. Alternatively, the sensor is stationary and the object is moved relatively to the sensor device to achieve multi-projection data acquisition. Another possibility is to rotate the detector around its axis in order to visualize hollow organs, or a combination thereafter with translation steps. If an array of sensors is employed, it can be arranged in a line-shaped geometry or a 2-dimensional or 3-dimensional pattern of detectors.

A signal collection device may be provided for collecting and storing the signals from the detectors. This device can be implemented in the time domain by recording signals over time and utilizing, for example, a Fourier transform or another time-frequency transformation, including wavelets or other bases, in order to convert the time measurements to frequency domain, i.e. amplitude and phase measurements in the generalized sense. Alternatively, the signal collection device can acquire signals directly in the frequency domain by recording amplitude and phase, for example after signal demodulation (using for instance a spectrum analyzer, homodyne and heterodyne detection such as the lock-in technique and/or IQ demodulation). Direct acquisition in the FD enables faster acquisition and less usage of memory of the image acquisition device. Acquisition in the time domain can record multiple frequencies and wavelengths with the same sampling device.

Preferably the arrangement of multiple illumination elements allows for homogeneous illumination of the sample. In the case of complex, irregularly shaped samples/targets, wave guides such as optical fibers or RF waveguides, antennas or coupling elements can be used to enable homogeneous illumination over the whole sample. The excitation is characterized in that, at least partially, it overlaps with the detection geometry (i.e. the sensitivity field of the transducer/acoustic sensor element/array) to allow for efficient thermoacoustic wave detection.

Detection will also operate, however, with focusing the energy in certain parts of the object to be measured. In this case, focusing enables positional certainty at least along two dimensions, whereas the third dimension can be captured as a phase-delay measurement. For example, in microscopic implementations or glucose monitoring applications of this technique, whereby the sensor can be arranged to collect only from a small area within the tissue.

The device and method according to the invention allows for detecting and/or determining amplitude information and/or phase information of the mechanical pressure wave/ultrasound signal. Amplitude and phase may, e.g., be measured using homodyne and/or heterodyne detection, for example employing a lock-in amplifier or using IQ demodulation techniques. Alternatively, a spectrum analyzer equivalent device can be used which measures amplitude and phase of the acoustic signal. In a further alternative, acoustic signals can be recorded in time domain while the (fast) Fourier transform (FFT) can be used to transform the signals into the frequency domain to get the amplitude and phase components of the thermoacoustic signal.

In order to measure signals in the frequency domain particularly efficiently, it is preferred to use the lock-in technique to provide a fast, ultrasensitive, and reliable method to accurately acquire phase and amplitude information of the thermoacoustic signals. Furthermore, utilization of dedicated lock-techniques with multiple demodulators resolves multiple frequencies simultaneously using one input channel, saving hardware resources and acquisition time.

Preferably, the region of interest of the object is homogeneously illuminated using at least one illumination device consisting of energy waveguides such as an optical fiber and/or an array of optical fibers (V-grooves), an antenna, a RF waveguide or energy coupling elements. The illumination can be arranged so that the sample is radiated on the outer surface at different positions around the sample or locations on the surface of the sample.

However, illumination can also be performed within the target using an endoscopic device. In this case, the illumination device excites the ROI within a hollow organ or a vessel while the detector device can be placed outside the ROI or also within the illuminated target and an endoscopic imaging device.

In frequency domain thermoacoustics the spectral component of the acoustic response of the tissue represents a "copy" of the modulation input of the exciting radiation. For example, when using light sources with an intensity modulation at frequency f, induced acoustic signals can be measured at the same frequency f. However, in the case of radiofrequency stimulation, acoustic signals are preferably induced at the second harmonic of the RF excitation field. For example, exposing tissue to a RF field resonating at f=1 MHz, acoustic signals will be induced at f=2 MHz. This is because the thermoacoustic pressure is proportional to local energy deposition of the applied field.

Due to the nonlinearity of RF generators, in addition to the fundamental frequency (i.e. the RF field resonating at frequency f) multiple harmonics are generated which interfere with the detection device, i.e. the transducer and the acquisition unit. These harmonics, particularly the second harmonic of the RF generator, significantly impede measuring the second harmonic of the acoustic signal.

To overcome this interference effect, it is preferred to use a differential measurement method which subtracts the interfering $2^{nd}$ harmonic of the RF source device from the detection device. Preferably, subtraction can be performed by simply applying an inverse field to the detection unit so that the $2^{nd}$ harmonic of the RF source device is calibrated to zero, thus enabling an interference free thermoacoustic signal measurement. For example, using an RF source emitting magnetic fields at frequency f, the second harmonic of the RF source can be eliminated by applying an inverse magnetic field at frequency 2f to the detector device (vector addition/superimposing magnetic vector fields).

Alternatively, the $2^{nd}$ harmonic of the source device can be eliminated by measuring the RF field strength (magnetic and/or electric field component) at a defined position and subtracting its contribution from the detector device using for example a differential amplifier. The measurement position can be next to the detector device or close to the sample or at a specific location within the radiation and detection geometry that allows for accurate measurement of the RF field.

Multifrequency stimulation using more than one RF excitation frequency can also be performed at RF energy levels. Moreover, in order to overcome RF interference, at least two sources can be used each emitting at different signals $sig_1=A_1 \sin(2\pi f_{RF,1} t)$ and $sig_2=A_2 \sin(2\pi f_{RF,2} t)$ By illuminating the target with the superimposed field of two different excitation frequencies, the tissue is excited with the signal $$sig_3 = sig_1 + sig_2 = 2A\sin\left(2\pi \frac{f_1+f_2}{2}t\right)\cos\left(2\pi \frac{f_1-f_2}{2}t\right).$$

Accordingly, the thermoacoustic signal will be generated at the frequencies $f_{TAS}=2f_1$, $f_{TAS}=2f_2$ and at the combination of those stimulation frequencies $f_{TAS}=f_1+f_2$. Similarly, stimulation can be extended to more than two sources where the thermoacoustic signal will be generated at frequencies represented by the harmonics of the stimulation frequency and linear combinations of excitation frequencies.

Unlike frequency mixing, the superposition of fields does not create new frequencies, so that the thermoacoustic signal (i.e. the amplitude and phase components at the frequency $f_{TAS}$) can be measured free of interference as compared to the single frequency (see previous paragraph).

In summary, an aspect of the invention provides for measuring amplitude and/or phase of thermoacoustic sources exposed to transient energy. To reconstruct images, amplitude and/or phase information are measured at multiple positions from the target. The amplitude of the signal represents data on the absorption properties of EME while the phase of the thermoacoustic signal contains information on the position of thermoacoustic sources in the ROI, but also includes information on the magnitude of the absorber. Thus, preferably both amplitude and phase are used for image reconstruction to resolve the location of thermoacoustic sources (i.e. absorbers of energy, particularly EME) quantitatively at high spatial resolution, although purely phase detection has also been shown to be capable to localize the sources even when amplitude is not measured or employed in the inversion. Surprisingly, it was also found that phase-only reconstructions, i.e. without using the amplitude information, also results in meaningful images. Nevertheless, the simultaneous use of amplitude and phase leads to even better defined inverse problems which can be solved under lower signal to noise measurement conditions. Tomographic imaging, utilizing data acquisition along multiple projections, provides high spatial resolution and better view of the measured target, yielding higher information content within the acquired data. Alternatively, thermoacoustic signals can also be measured according to a line scan (raster scan or x-y scan) where the measurement geometry does not allow for tomographic detection. In this case, a single element transducer or an array of ultrasound sensors are moved on the target surface, measuring thermoacoustic signals in a point-by-point fashion (raster scanning of samples).

Figure 2:
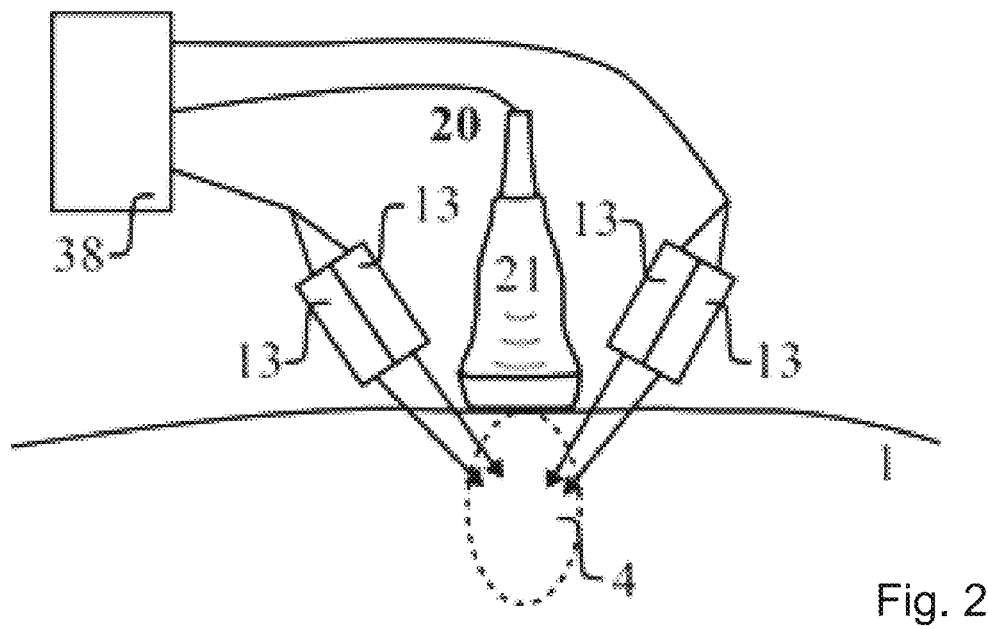
Figure 3:
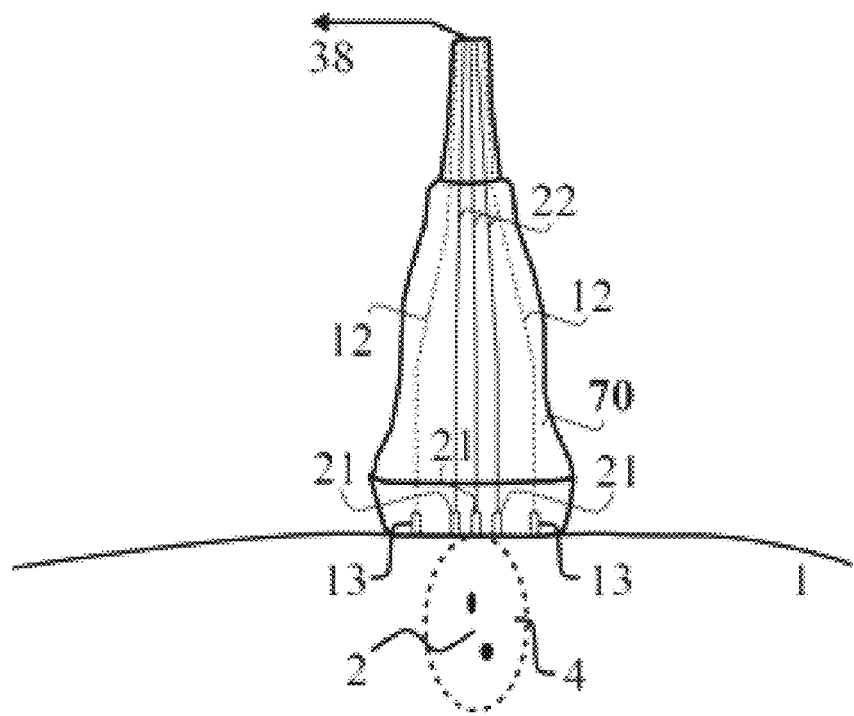
Figure 4:
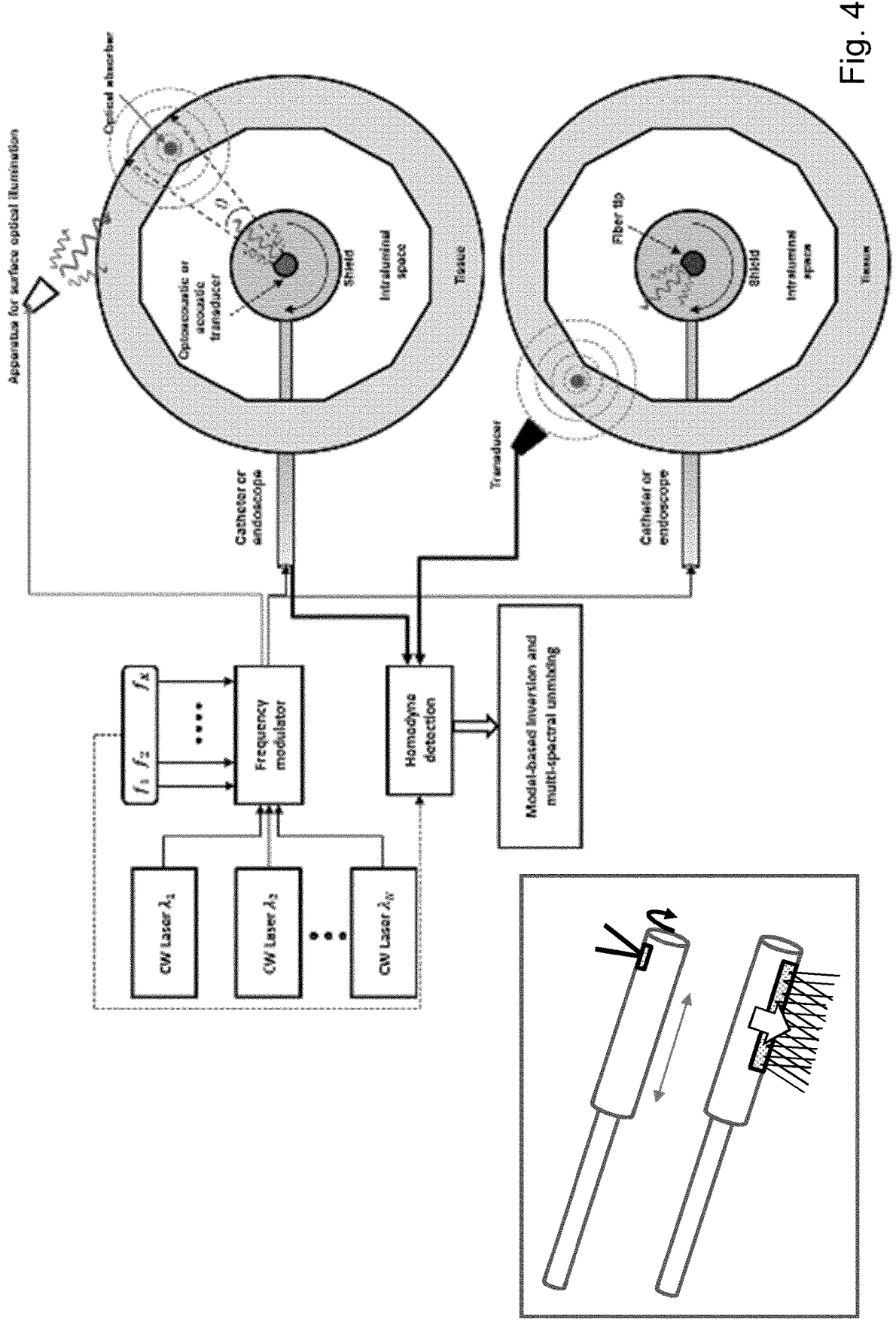
Figure 5:
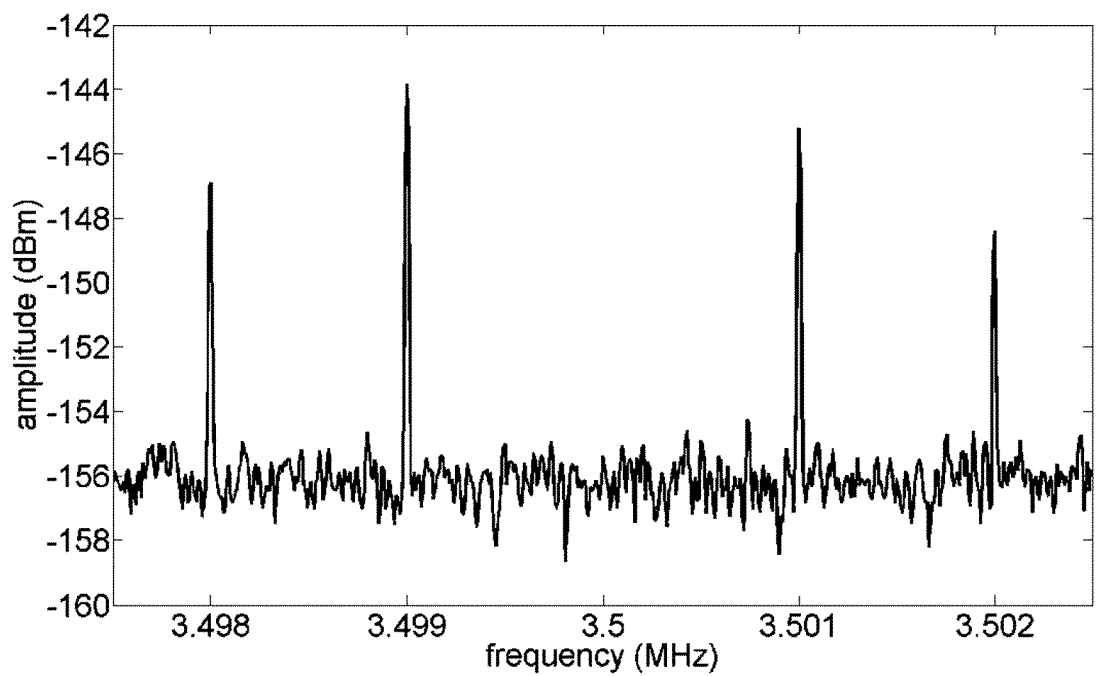

The above and other elements, features, characteristics and advantages of the present invention will become more apparent from the following detailed description of preferred embodiments with reference to the attached figures showing:

FIG. 1 an example of a device for thermoacoustic sensing or imaging;

FIG. 2 an example of a device which is particularly adapted for skin imaging;

FIG. 3 an example of an integrated handheld device;

FIG. 4 an example of a device which is particularly adapted for endoscopic imaging, the insert showing embodiments of a fiber tip;

FIG. 5 a diagram of detected acoustic waves in the Fourier domain; and

Figure 6:
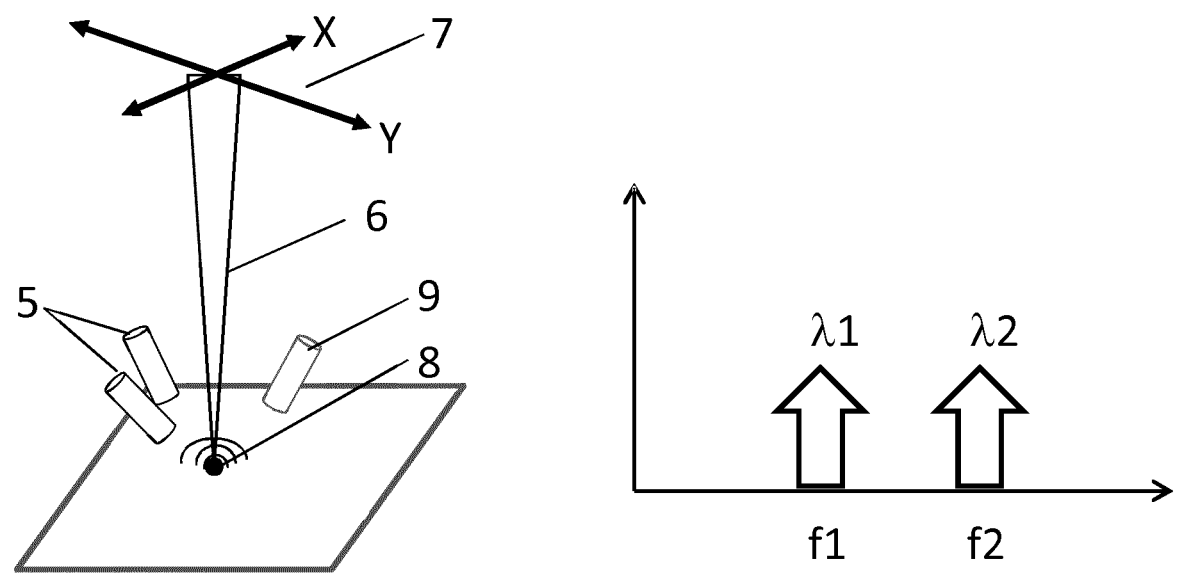

FIG. 6 a schematic representation of an example of a device configured to implement imaging based on the geometrical characteristics of the energy emitted (left part) and a schematic representation of the illumination signal (right part).

FIG. 1 shows a schematic representation of an example of a device 100 for thermoacoustic sensing comprising a source device 10 configured to emit transient electromagnetic radiation and/or particle radiation and a detector device 20 configured to detect acoustic waves generated in a sample 1 upon irradiation with the emitted electromagnetic radiation and/or particle radiation.

The device 100 further comprises a data acquisition and processing device 30 configured to process thermoacoustic signals corresponding to the detected acoustic waves and to derive at least one property of the sample 1 based on the processed thermoacoustic signals.

Moreover, the device 10 comprises a control/modulation device 40, a sample holder 50 configured to receive and/or hold the sample 1, and a motion device 60 configured to generate a rotational and/or translational motion of the sample 1, on the one hand, and the source device 10 and/or detector device 20, on the other hand, relative to each other.

The source device 10 comprises at least one source 11 emitting transient energy. Preferably, the source 11 comprises a light source, such as a laser source or a light emitting diode (LED). The light source provides the ability to emit intensity modulated illumination patterns at predefined frequencies consecutively or simultaneously by superimposing driving signals at multiple discrete frequencies. Dependent on the desired application, the source 11 can also be a radiofrequency (RF) or microwave source.

Transient energies in the form of light, RF waves or microwaves, respectively, are coupled to the sample 1 preferably by means of waveguides 12, comprising an optical fiber, a RF waveguide or cable, an antenna, or mirrors, respectively. To achieve homogeneous illumination, the sample 1 is illuminated from multiple angles using energy couplers 13.

For example, as the source 11 a laser array is provided which is configured to emit light at three wavelengths at 680 nm, 780 nm and 860 nm. Further, as the detector device 20 an acoustic wave detector with a central frequency of 7.5 MHz and a cut-off frequency of 11 MHz is provided.

Frequency domain multispectral optoacoustic tomography (FD-MSOT) is performed, for example, by using three groups of modulation frequencies with five frequencies per group, i.e. group $\lambda_1$ at 680 nm:

$f_{680}$=5.1 MHz, 6.1 MHz, 7.1 MHz, 8.1 MHz, 9.1 MHz, 10.1 MHz, group $\lambda_2$ at 780 nm:
$f_{780}$=5.3 MHz, 6.3 MHz, 7.3 MHz, 8.3 MHz, 9.3 MHz, 10.3 MHz, and group $\lambda_3$ at 860 nm:
$f_{860}$=5.5 MHz, 6.5 MHz, 7.5 MHz, 8.5 MHz, 9.5 MHz, 10.5 MHz.

It has to be noted that the frequency shift in each modulation group is not limited to 1 MHz but can also be lower than 1 MHz or higher than 1 MHz.

Furthermore, the frequency deviation from one group to the other (in the above given example: $\Delta f_{680\_780}$=0.2 MHz) can also be lower ($\Delta f_{680\_780}$<0.2 MHz) or higher ($\Delta f_{680\_780}$>0.2 MHz) on the condition that the spectral component of the stimulation frequency of wavelength $\lambda_x$ can be resolved from the stimulation frequency of wavelength $\lambda_y$. Moreover, the number of frequencies per group is not limited to five but can also be lower or higher.

Thus, the FD-MSOT device 100 is configured to perform real time and simultaneous visualization of at least one, but preferably several biomarkers and/or EME absorbers in tissue at high resolution using backprojection and/or model based reconstruction methods combined with spectral unmixing algorithms.

The detector device 20 is adapted to measure mechanical stress waves, in particular ultrasound signals, emanating from thermoacoustic sources, i.e. absorbers of transient energy, particularly electromagnetic energy. In the present example, the detector device 20 comprises a single element transducer 21 which can be rotated around the object 1 using the motion device 60. Alternatively or additionally, similar to ultrasound imaging, an array of acoustic sensors with multiple sensing elements (e.g. 64, 128, 256 elements or more) is preferably used to detect thermoacoustic signals. The ultrasound detector is advantageously based on PZT/PVdF technology or on CMUT (capacitive micromachined ultrasonic transducers) technology; alternatively or additionally, optical detection methods based on interferometry can also be employed to sense mechanical pressure waves.

Preferably, the detection bandwidth of the detector device 20 is matched to the size of absorbers within the imaged ROI and also the modulation frequencies of the source device 10.

The acquisition and processing device 30 is adapted to measure amplitude 33 and phase 34 components (or complex numbers) of the generated thermoacoustic signals. Preferably, homodyne/heterodyne detection by means of a lock-in amplifier 32 is employed where the detection unit is locked to the reference frequency provided by the control unit 40. Amplitude 33 and phase 34 components are decomposed by the lock-in detector and stored in a storage unit 35 before the image reconstruction device 36 generates a thermoacoustic image.

Alternatively to the lock-in amplifier 32, a spectrum analyzer 32 can be utilized to resolve amplitude and phase components of the thermoacoustic signal. Furthermore, amplitude 33 and phase 34 components of the thermoacoustic signals can be retrieved by measuring signals over time. In this case, transformation in the Fourier domain yields the phase 34 and amplitude 33 of the signal. Further alternatively, an IQ demodulator can be used to measure the amplitude and phase of the optoacoustic signal.

Optionally, thermoacoustic signals are pre-amplified using a low noise amplifier 31.

The image reconstruction device 36 is adapted to generate images of absorption of transient energy within a region of interest. Preferably, the reconstruction device 36 is configured to model the illumination and detection geometry and to perform dedicated inversion algorithms to produce a quantitative tomographic image showing a representative map of energy absorbers. Modeling includes a photon propagation model, the size of detectors and acoustic heterogeneities within the ROI.

Reconstructed images 4 of the ROI, i.e. absorbers 2 and 3 with different absorption characteristics can be displayed on an output device 37 such as a screen, a printer, a computer, or a data storage device.

The control device 40 comprises a signal generator (for example a function generator or an arbitrary waveform generator) 41 configured to drive the source device 10 with predetermined modulation frequencies. In the case of optical excitation, the source device 10 can be based on a driver providing a modulated current which drives a laser diode, LED etc. Alternatively, the intensity of EME can be modulated by means of an acousto-optic modulator AOM. Preferably, the control device 40 is configured to provide signals at discrete and/or distinct modulation frequencies consecutively; as an example, the signal generator 41 drives the source device 11 with a sinusoidal signal at multiple frequencies, i.e. starting in discrete steps from $f_1$=1 MHz reaching $f_5$=5 MHz with $\Delta f$=MHz frequency steps. At each discrete frequency step, the acquisition and processing device 30 measures amplitude and phase components of the signal.

Alternatively, the control device 40 is configured to generate signal patterns containing multiple frequency components simultaneously. This is achieved by signal combiners/adders or arbitrary waveform generators to yield a superimposed signal with multiple spectral (phase and amplitude) components.

The sample 1 is fixed on a dedicated carrier unit 50 which enables immobilizing the sample during the experiment. The carrier unit 50 further enables exact positioning of the sample 1 in the imaging setup. Preferably, to acquire a tomographic data set, either the detection unit 20 is rotated with a rotation stage 62 around the object 1, or the object 1 is rotated. The motion stage 60 is controlled by a motion controller 61 and synchronized with the data acquisition unit 30.

FIG. 2 shows an example of a device which is particularly adapted for skin imaging. The illumination devices 13 and the detector device 21 are arranged outside the object 1 which is illuminated with, preferably, two or more wavelengths to perform frequency domain multispectral imaging at several wavelengths including multiple modulation frequencies.

The detector element 21 can be a single element transducer but, preferably, comprises an array of transducers to acquire acoustic signals simultaneously over multiple projection angles or positions across the object 1. The detector 21 and the illumination devices 13 are connected to a casing 38 of the FD-MSOT device where signals are optionally pre-amplified, acquired and stored for further processing and visualization. The FD-MSOT approach allows for illuminating the object 1 at several wavelengths at different groups of modulation frequencies to achieve real-time scanning of skin diseases.

The object 1 can be scanned at multiple different angles around the object 1 (tomographic signal acquisition) or according to a raster scanning method where the sample 1 is imaged at different x-y positions (x-y-horizontal scanning). Furthermore, the detection can be performed by translating and/or rotating the illumination/sensing unit 13/21 (combination of raster scanning with signal detection at multiple projections) to extend the field of view.

Preferably, the device can be adapted for imaging on multiple scales, i.e. on the macroscopic, mesoscopic and microscopic scale, simultaneously or independently.

When used as a microscopic FD-MSOT device, the detection unit 21 comprises a high frequency ultrasound detector (single element or array) which is preferably based on PZT/PvdF/CMUT technology, but can also be a mechanical pressure sensor which is based on interferometry, e.g. a Fabry-Perot or a Fiber Bragg grating based ultrasound sensor. Illumination is provided by multiple (at least one) illumination units 13 each encoded with a specific group of modulation frequencies as described above.

Advantageously, different imaging scales can also be combined. As an example, the EME/laser can be modulated at two different frequency groups in the low-MHz region for macroscopic imaging $\lambda_{1,macroscopic}$:
$f_{1,macroscopic}$=5.1 MHz, 6.1 MHz, 7.1 MHz, 8.1 MHz, 9.1 MHz, 10.1 MHz,
while simultaneously driving the laser with a higher frequency group
$\lambda_{2,macroscopic}$:
$f_{2,macroscopic}$=80 MHz, 81 MHz, 82 MHz, 83 MHz, 84 MHz, 85 MHz,
for microscopic imaging in real time. In this case, two different detectors with a detection bandwidth matching the modulation frequencies $f_{1,macroscopic}$ and $f_{2,macroscopic}$ are employed.

Similarly, mesoscopic and microscopic imaging can be combined by using different groups of excitation frequencies.

Regarding further components, features and functionalities of the device shown in FIG. 2, the elucidations with reference to FIG. 1 apply accordingly.

FIG. 3 shows an example of an integrated handheld device in which components of the device are integrated in a measuring head 70. The measuring head 70 comprises illumination devices 13 and detection devices 21, which are connected to the remote device casing 38 by optical fibers 12 or cables 22, respectively. The measuring head 70 can be manually moved across the object 1 for scanning the ROI in the target 4 to excite absorbers of EME sources and detect corresponding acoustic signals from these sources in real time. Regarding further components, features and functionalities of the handheld device shown in FIG. 3, the elucidations with reference to FIG. 1 apply accordingly.

FIG. 4 shows an example of a device which is particularly adapted for endoscopic imaging, wherein the above-mentioned approach of frequency domain thermoacoustics is applied to imaging of hollow regions. In the present example, continuous-wave (CW) laser light at various wavelengths $\lambda_1, \ldots, \lambda_N$ is modulated at K frequencies $f_1, \ldots, f_K$. The tissue can be excited using each wavelength, simultaneously modulated with the K frequencies.

As apparent from exemplary implementations shown in the upper right part of FIG. 4, an illumination and detection can be combined in one catheter and/or endoscope tip to perform imaging within the hollow region, e.g. within an organ or within a vascular system. Alternatively and/or additionally, the ROI within the object can be illuminated via the surface from outside the tissue while acoustic signals are measured using a detection device in form of an optoacoustic or acoustic transducer located within the target.

As apparent from another exemplary implementation shown in the lower right part of FIG. 4, an illumination, e.g. by means of fiber tip, can be arranged within the target while the acoustic sensor, e.g. an ultrasound transducer, is placed outside the tissue.

Preferably, the catheter and/or endoscope transducer tip moves in the intraluminal space using a certain pattern, e.g. a spiral shape, where at each location and angle the acoustic wave generated by the optical absorber is detected with a given angular window of θ. The data collected across all frequencies and wavelengths is then processed using model-based or backprojection algorithms. Un-mixing methods are used to separate concentration from different biomarkers.

By means of the exemplary implementations illustrated in FIG. 4 frequency-domain multi-spectral intravascular imaging and endoscopy is possible, wherein multiple wavelengths are simultaneously modulated by a group of discrete frequencies. The modulated light is then used to illuminate the tissue, either from the catheter/endoscope tip using an optoacoustic transducer or from the surface. The acoustic signal detected using a limited-view acoustic transducer is then converted to amplitude and phase information using a detection approach (such as homodyne detection). Data collected across all frequencies and wavelengths is then processed by model-based or backprojection algorithms using un-mixing of multispectral information.

FIG. 5 shows an example of a diagram of detected acoustic waves in the Fourier domain, in which the amplitudes of the detected acoustic waves are plotted versus frequency.

The results shown in FIG. 5 were obtained when illuminating an optical absorber with an illumination pattern consisting of a superimposed signal at multiple, in the present example four, discrete frequencies (i.e. a group of multiple frequencies).

FIG. 6 shows a schematic representation of an example of a device implementing imaging based on the geometrical characteristics of the energy emitted. In this case a conditioned light beam 6, e.g. a focused or a collimated light beam, is scanned in at least two dimensions by a scanning device 7 (alternatively the target 8 can be scanned). The beam 6 generates optoacoustic contrast within the scanned target 3. The acoustic waves generated are captured by one 9 or multiple 5 acoustic detectors. While in the present example single detectors are shown, the optoacoustic signal collection system can e.g. be a conical lens, an array for acoustic detectors, an interferometric method or any other means of collecting and detecting sound waves. The graph on the right represents the illumination signal, consisting in this case of two frequencies f1 and f2, each one carrying at different wavelength λ1 and λ2, respectively. Correspondingly, the two wavelengths can be simultaneously emitted and their relative absorption-based ultrasonic signals separated by frequency decomposition of the detected acoustic wave.

In the present example, the absorber consisted of a 350 μm graphite rod which was illuminated by an intensity modulated laser of a single wavelength of 808 nm (Omicron Laserage Laserprodukte, GmbH, Germany, Model: Omicron A350). Acoustic signals are detected with a cylindrically focused single element PZT ultrasound sensor (Olympus NDT, Waltham, Mass., USA, Model: V382, central frequency: 3.5 MHz, bandwidth: 76%).

In this case, the illumination pattern consisted of four different modulation frequencies at $f_1$=3.49 MHz, $f_2$=3.51 MHz, $f_3$=3.48 MHz and $f_4$=3.52 MHz. As apparent from the diagram, the amplitude of the optoacoustic signal shows clearly spectral components at each modulation frequency.

Although the phase of the detected acoustic waves is not shown in the present diagram, the above elucidations regarding amplitude also apply to the phase of the detected acoustic waves the Fourier domain accordingly.

Based on the values of the amplitude and/or the phase of each of the components at the distinct frequencies ($f_1$, $f_2$, $f_3$, $f_4$) of the intensity modulation of the laser light, at least one property, e.g. an absorption or absorption map, of the ROI is derived.

In the following, preferred applications of the device and method according to the invention are described in more detail.

A preferred application of the invention is in the biological and medical field for imaging, diagnosis, therapy, and treatment of humans and animals or part of humans and animals in-vivo, ex vivo and in vitro. However, the invention can also be applied in the industrial, environmental and geological field, for example for testing of specific properties of various materials (such as absorption, nondestructive testing, testing material deficiencies and so on).

Of particular interest is the application of the present FD thermoacoustic imaging method in biological and medical imaging. Preferably, the invention can be used as a clinical diagnosis tool to image cancer, inflammations, cardiovascular diseases, skin diseases, neurodegenerative diseases, metabolic diseases, anomalies in tissue vasculature. Furthermore, the invention can be used for neurological imaging and to monitor tissue growth, for tumor staging.

Since FD-MSOT enables real-time visualization of multiple biomarkers simultaneously, the invention provides further powerful applications for video-rate tracking of tissue intrinsic absorbers (hemoglobin, melanin cells) as well as exogenously applied contrast agents. Thus, FD-MSOT can be applied to determine oxygenation levels in real time and track the pathway of multiple injected agents simultaneously.

The device can further be applied to determine the oxygenation levels of blood using different energy levels of the EME (such as light at different wavelengths, RF at different frequencies etc.). Particularly in the optical regime, the device can be utilized for imaging of hemodynamic processes and hematologic diseases. As blood in its oxy- and deoxygenated state have different absorption characteristics at different wavelengths, the measured opto/thermoacoustic signals can be used to determine the level of oxy and deoxy blood.

The real time imaging capability of the present device and method coupled with simultaneous multispectral illumination allows for accurate tracking of physiological and molecular changes of tissue in vivo. Thus, intrinsic absorption changes at different wavelengths can be tracked, such as blood perfusion, hemoglobin, melanin, and other tissue intrinsic absorbers.

Furthermore, applying extrinsic contrast agents/contrast enhancers, organ perfusion can be tracked at real time, yielding physiological and molecular information in vivo.

The invention can also be applied as an endoscopic device where the detector and the illumination device are arranged so that imaging is performed within the tissue/hollow organ. Thus, at least one of the detection unit and the source unit is adapted such that it is inserted inside hollow organ or a blood vessel, for intracavity imaging such as intravascular imaging, imaging of the colon, imaging of the gastrointestinal track, transurethral imaging and so on. Furthermore, the illumination device can be inserted within the tissue to excite tissue from within the ROI while detection of acoustic signals is performed on the surface of the tissue.

Alternatively, the detector is placed within the tissue while illumination is performed on the surface of the ROI.

Depending on the stimulation, i.e. modulation, frequency, the proposed invention can be used for imaging on the macroscopic, mesoscopic and microscopic scale. Using low excitation frequencies in the range of few MHz (up to ~15 MHz), the device is advantageously applied to image absorbers on the macroscopic scale allowing for resolutions in the range of 100 µm. Utilizing higher stimulation frequencies, the invention can be applied on the mesoscopic scale (15 MHz<f<50 MHz), combining high resolution with high penetration depths. At higher frequencies (f>50 MHz), the invention can be applied for microscopic imaging. #

It is to be noted that the invention also allows for simultaneous imaging at different scales. By using different detection devices, the device can be applied for macroscopic and/or mesoscopic and/or microscopic imaging of the same sample at the same time.

Particularly, the combination of mesoscoplc and microscopic imaging can be used to image skin diseases and for tumor staging.

The inventive device and method can furthermore be applied in non-biological, industrial environments to screen food and drink. Using different energy levels of EME (light, RF, X-rays and so on), materials can be tested according to their absorption and or material deficiencies.

Furthermore, the device can be applied in geological settings to image soil or for screening of biological plants.

What is claimed is:

1. A device for thermoacoustic sensing, the device comprising:
   a) an irradiation unit comprising an electromagnetic radiation source or a particle beam source, the irradiation unit being configured to:
      generate electromagnetic or particle radiation, respectively,
      modulate an intensity or frequency of the electromagnetic or particle radiation, respectively, with a first modulation, the first modulation simultaneously comprising at least two modulation components, wherein each modulation component is a periodic modulation at a distinct frequency, wherein the at least two modulation components of the first modulation are concurrently emitted, and wherein the first modulation corresponds to a superposition of the at least two modulation components, and
      continuously emit the modulated electromagnetic or particle radiation, respectively, towards a target so that the at least two modulation components at the distinct frequencies impinge upon the target at the same time, whereby acoustic waves are continuously generated in the target, the acoustic waves exhibiting a second modulation, the second modulation simultaneously comprising acoustic wave components at the distinct frequencies of the at least two modulation components or at harmonic frequencies of the distinct frequencies of the at least two modulation components,
   b) a detection unit comprising one or more sensors, the detection unit configured to simultaneously detect the acoustic waves exhibiting the second modulation while the modulated electromagnetic or particle radiation, respectively, is being continuously emitted towards the target, and
   c) a processing device configured to determine thermoacoustic values of at least one of an amplitude and a phase of each of the acoustic wave components at the distinct frequencies of the at least two modulation components or at harmonic frequencies of the distinct frequencies of the at least two modulation components.

2. The device according to claim 1, the processing device being configured to derive at least one property of the target based on the determined thermoacoustic values of at least one of the amplitude and the phase.

3. The device according to claim 2, the at least one property of the target relating to an absorption of the continuously emitted electromagnetic or particle radiation by the target.

4. The device according to claim 2, the at least one property of the target relating to an image or a map of a spatial distribution of the at least one property of the target.

5. The device according to claim 1, wherein the second modulation corresponds to at least one of:
   a. a modulation of the intensity or the frequency of the continuously generated acoustic waves, and
   b. a modulation comprising a linear combination of two or more frequencies contained in the first modulation.

6. The device according to claim 1, the first modulation or the second modulation corresponding to a periodic modulation of the continuously emitted electromagnetic or particle radiation or the continuously generated acoustic waves, respectively.

7. The device according to claim 1, the first modulation or the second modulation exhibiting a rectangular, triangular or sawtooth shape.

8. The device according to claim 1, the modulation components corresponding to two or more sinusoids at the distinct frequencies.

9. The device according to claim 8, the first modulation corresponding to a sum of the two or more sinusoids at the distinct frequencies.

10. The device according to claim 2, wherein the distinct frequencies of the at least two modulation components of the first modulation or the distinct frequencies of the two or more acoustic wave components of the second modulation are in a frequency range according to at least one of the following conditions:
   if the distinct frequencies are below 15 MHz, then the at least one property shall be determined within a first maximum sensing depth within the target;
   if the distinct frequencies are in a frequency range between 15 MHz and 50 MHz, then the at least one property shall be determined within a second maximum sensing depth within the target, the second maximum sensing depth being smaller than the first maximum sensing depth;
   if the distinct frequencies are above 50 MHz, then the at least one property shall be determined within a third maximum sensing depth within the target, the third maximum sensing depth being smaller than the second maximum sensing depth; and
   the distinct frequencies are in a frequency range corresponding to a detection bandwidth of the detection unit.

11. The device according to claim 1, the irradiation unit being configured to emit the electromagnetic or particle radiation at two or more different wavelengths.

12. The device according to claim 11, the irradiation unit being configured to emit the electromagnetic or particle radiation consecutively or simultaneously at the two or more different wavelengths, the electromagnetic or particle radiation at each of the two or more different wavelengths exhibiting a first modulation consisting of two or more modulation components at distinct frequencies.

13. The device according to claim 1, the detection unit configured to detect the acoustic waves, which are generated in the target while the electromagnetic or particle radiation exhibiting the first modulation is being emitted towards the target, at two or more different positions around the target.

14. The device according to claim 13, the detection unit configured to detect the acoustic waves at two or more different positions located on at least one of a straight line, a circular line, and a cylindrically shaped area around the target.

15. A method for thermoacoustic sensing, the method comprising:
   a) continuously emitting electromagnetic or particle radiation, respectively, exhibiting a first modulation simultaneously comprising at least two modulation components, wherein each modulation component is a periodic modulation at a distinct frequency, towards a target so that the at least two modulation components at the distinct frequencies impinge upon the target at the same time, wherein the first modulation corresponds to a superposition of the at least two modulation components such that the at least two modulation components of the first modulation are concurrently emitted, whereby acoustic waves are continuously generated in the target, the acoustic waves exhibiting a second modulation, the second modulation simultaneously comprising acoustic wave components at the distinct frequencies of the at least two modulation components or at harmonic frequencies of the distinct frequencies of the at least two modulation components,
   b) simultaneously detecting the acoustic waves exhibiting the second modulation while the electromagnetic or particle radiation exhibiting the first modulation is continuously emitted towards the target, and
   c) determining thermoacoustic values of at least one of an amplitude and a phase of each of the acoustic wave components at the distinct frequencies of the at least two modulation components or at the harmonic frequencies of the distinct frequencies of the at least two modulation components.

16. A device for thermoacoustic sensing, the device comprising:
   a) an irradiation unit comprising an electromagnetic radiation source or a particle beam source, the irradiation unit being configured to:
      generate electromagnetic or particle radiation, respectively,
      modulate an intensity or frequency of the electromagnetic or particle radiation, respectively, with a first modulation, the first modulation simultaneously comprising at least two modulation components at distinct frequencies, and
      continuously emit the modulated electromagnetic or particle radiation, respectively, towards a target so that the at least two modulation components at the distinct frequencies impinge upon the target at the same time, wherein each modulation component is a periodic modulation at a distinct frequency, wherein the at least two modulation components of the first modulation are concurrently emitted and the first modulation corresponds to a superimposition of the at least two modulation components, whereby acoustic waves are continuously generated in the target, the acoustic waves exhibiting a second modulation, the second modulation simultaneously comprising acoustic wave components at the distinct frequencies of the at least two modulation components or at harmonic frequencies of the distinct frequencies of the at least two modulation components, b) a detection unit comprising one or more sensors, the detection unit configured to simultaneously detect the acoustic waves exhibiting the second modulation while the modulated electromagnetic or particle radiation, respectively, is being continuously emitted towards the target, whereby the acoustic wave components at the distinct frequencies of the at least two modulation components or at harmonic frequencies of the distinct frequencies of the at least two modulation components are detected at the same time, and c) a processing device configured to determine at least one thermoacoustic value of at least one of an amplitude and a phase of each of the acoustic wave components at each of the distinct frequencies of the at least two modulation components or at each of the harmonic frequencies of the distinct frequencies of the at least two modulation components.

* * * * *